United States Patent [19]

Tom-Moy et al.

[11] Patent Number: 5,527,711
[45] Date of Patent: Jun. 18, 1996

[54] METHOD AND REAGENTS FOR BINDING CHEMICAL ANALYTES TO A SUBSTRATE SURFACE, AND RELATED ANALYTICAL DEVICES AND DIAGNOSTIC TECHNIQUES

[75] Inventors: May Tom-Moy, San Carlos; Joel Myerson, Berkeley; Karla M. Robotti, Foster City, all of Calif.

[73] Assignee: Hewlett Packard Company, Palo Alto, Calif.

[21] Appl. No.: 167,273

[22] Filed: Dec. 13, 1993

[51] Int. Cl.⁶ ................................................. G01N 33/53
[52] U.S. Cl. .................. 436/518; 204/403; 422/82.01; 422/82.11; 435/7.5; 435/962; 436/151; 436/528; 436/543; 436/807; 436/822; 548/304.1
[58] Field of Search ................................ 427/2, 214, 220, 427/331, 414, 2.11; 435/7.5, 962; 422/57, 82.01–82.08, 82.11; 436/151, 518, 528, 543, 807, 822; 204/403, 153.12; 73/DIG. 4; 530/807; 548/304.1

[56] References Cited

U.S. PATENT DOCUMENTS

| | | | |
|---|---|---|---|
| Re. 31,712 | 10/1984 | Giese | 428/407 |
| 4,478,914 | 10/1984 | Giese | 428/407 |
| 4,530,786 | 7/1985 | Dunbar et al. | 436/532 X |
| 4,803,170 | 2/1989 | Stanton et al. | 436/518 |
| 4,847,209 | 7/1989 | Lewis et al. | 436/533 |
| 4,952,519 | 8/1990 | Lau | 436/532 |
| 4,999,284 | 3/1991 | Ward et al. | 435/4 |
| 5,028,535 | 7/1991 | Buechler et al. | 435/7.1 |
| 5,130,257 | 7/1992 | Baer et al. | 436/151 |
| 5,145,790 | 9/1992 | Mattingly et al. | 436/536 |
| 5,147,786 | 9/1992 | Feng et al. | 435/7.94 |
| 5,156,810 | 10/1992 | Ribi | 422/82.01 |
| 5,156,972 | 10/1992 | Issachar | 435/288 |
| 5,168,057 | 12/1992 | Oh et al. | 435/174 |
| 5,200,346 | 4/1993 | Friedman et al. | 436/518 |
| 5,219,764 | 6/1993 | Huber et al. | 436/536 |
| 5,229,301 | 7/1993 | Spira-Solomon | 436/518 |
| 5,236,830 | 8/1993 | Ishikawa | 435/7.5 |
| 5,283,342 | 2/1994 | Gustavson et al. | 548/304.1 |
| 5,306,644 | 4/1994 | Myerholtz et al. | 436/149 |
| 5,334,528 | 8/1994 | Stanker et al. | 435/240.27 |
| 5,391,272 | 2/1995 | O'Daly et al. | 204/153.12 |

FOREIGN PATENT DOCUMENTS

| | | |
|---|---|---|
| 396116 | 11/1990 | European Pat. Off. . |
| 416730 | 3/1991 | European Pat. Off. . |

OTHER PUBLICATIONS

E. Ishikawa et al, "Novel and Sensitive Noncompetitive (Two–Site) Immuno Assay for Haptens . . . " in Clin. Biochem. 23(5): 445–453 (Oct. 1990).

L. Wofsy, "Methods and Applications of Hapten–Sandwich Labeling" in Methods in Enzymology vol. 92: 472–488 (1983).

M. Wilchek et al., in "The Avidin–Biotin Complex in Bioanalytical Applications", *Anal. Biochem.* 171: 1–32 (1988).

*Primary Examiner*—Carol A. Spiegel

[57] ABSTRACT

A method is provided for detecting an analyte of interest in a sample. The method involves binding the analyte to the surface of a substrate through a biotin-biotin binding protein interaction, contacting the surface-bound analyte with a quantitatively detectable analyte-binding moiety that binds thereto, measuring the quantity of detectable moiety bound to the substrate surface and deriving therefrom the quantity of analyte in solution. A preferred use for the present method is in conjunction with a piezoelectric surface transverse wave device. Novel reagents useful for carrying out the inventive method are provided as well.

23 Claims, 2 Drawing Sheets

METHOD AND REAGENTS FOR BINDING CHEMICAL ANALYTES TO A SUBSTRATE SURFACE, AND RELATED ANALYTICAL DEVICES AND DIAGNOSTIC TECHNIQUES

TECHNICAL FIELD

This invention relates generally to chemical methods for detecting an analyte of interest in a sample. More specifically, the invention relates to a novel method for binding an analyte to the surface of a substrate so as to enable detection of the analyte thereon. The invention additionally relates to novel reagents and devices useful for carrying out the aforementioned method.

BACKGROUND

Many methods are known for detecting analytes of various kinds using a reactive solid surface. In many hybridization assay formats, for example, a label is detected on the surface of a substrate, e.g., on a glass or plastic bead, plate, tube or the like, to indicate the presence and/or quantity of an analyte of interest. There are also many types of chromatographic procedures in which reactive surfaces are used to facilitate the separation and/or detection of different types of analyte molecules. In still another context, mass biosensors are used to measure microquantities of biological materials, and, as with the aforementioned contexts, involve the use of a modified surface which selectively binds a particular component. Although the present invention is adaptable to a wide variety of contexts, it is particularly suited to use in conjunction with such mass biosensors.

As explained in commonly assigned U.S. Pat. No. 5,130,257 to Baer et al., European Patent Publication No. 416,730, inventors Tom-Moy et al., and co-pending U.S. Patent application Ser. No. 08/041,662, filed Apr. 1, 1993 (entitled "A Mass Sensor for Measuring Analytes in a Sample," inventors C. A. Myerholtz et al.), a preferred type of mass biosensor uses a piezoelectric crystal as an acoustic waveguide. Selective mass detection with such devices is achieved by coating the surface of the device with a chemically reactive layer that preferentially reacts with the substance to be detected such that the mass present on the reactive layer changes proportionately, i.e., relative to the amount of the substance to be detected. These devices thus function as chemical sensors that can measure the concentration of analytes in a solution into which the detector is immersed. For example, and as explained in U.S. Patent application Ser. No. 08/041,662, cited above, piezoelectric surface wave devices have been used to measure the concentration of a specific antibody in solution using a conventional assay format, as follows. The mass-sensitive surface of the device is coated with a receptor layer which contains the antigen corresponding to the antibody. The device is then exposed to a sample solution, and antibody present in the solution will bind to the surface of the device, thereby increasing the mass loading of the upper surface. An input transducer generates a periodic acoustic wave from a periodic electrical input signal. Radio frequency energy coupled into the device through the input transducer is converted to a surface acoustic wave confined to within a few wavelengths of the surface. The velocity of the surface acoustic wave will vary according to the mass loading on the top surface of the device. The surface acoustic wave propagates along the surface of the device until it encounters the output transducer, which converts the surface acoustic wave back into radio frequency energy. The change in propagation velocity of the surface acoustic wave corresponds to the mass bound to the surface of the crystal. By monitoring the frequency or relative phases of the input and output electrical signals, the mass changes at the surface of the crystal can be measured. Such acoustic waveguide devices can utilize different wave motions, including surface transverse waves (STWs), Rayleigh waves (SAWs), Lamb waves, and surface-skimming bulk waves (SSBWs), although STW devices are preferred.

The present invention makes use of the strong interaction between biotin and a biotin-binding protein to bind analyte molecules to the surface of a substrate, such as the surface of a piezoelectric crystal in a surface transverse wave biosensor. The use of the extremely high affinity ($K_a \approx 10^{15}$ $M^{-1}$), although noncovalent, bond formed between biotin and the biotin-binding protein avidin has been well-documented. M. Wilchek et al., in "The Avidin-Biotin Complex in Bioanalytical Applications," *Anal. Biochem.* 171:1–32 (1988), present an overview of a number of contexts within which the avidin-biotin complex has proven useful. There are additional references which propose the use of the avidin-biotin interaction in binding materials to surfaces. PCT Publication No. WO91/07087, for example, describes a technique for creating regions on a solid surface which are capable of selectively immobilizing an "anti-ligand" through biotin-avidin complexation. U.S. Pat. No. 4,952,519 and European Patent Publication No. 396,116 relate to the derivatization of the surface of a solid support so as to bind biotin or avidin thereto; PCT Publication No. WO88/04777 also describes an analyte detecting device containing a detection surface on which avidin or biotin is immobilized, while U.S. Pat. No. 4,478,914 and U.S. RE31,712, both to Giese, describe a modified surface coated with alternating layers of a ligand-binding protein such as avidin and a reactive ligand extender such as biotin. Commonly assigned European Patent Publication No. 416,730, cited previously, describes a mass biosensor in which a ligand-binding layer such as an avidin coating is provided on the piezoelectric crystal surface of the device, on top of which is provided a ligand-bearing coating such as a layer of biotinylated antibody.

Although a number of references thus describe the use of biotin-avidin complexation in a variety of analyte detection and quantitation procedures, none provide a method for attaching low molecular weight analytes—such as environmental analytes of interest—to a solid phase surface using biotin-avidin complexation. Typically, as noted above, biotin has been attached to large molecules such as protein and nucleic acid moieties. It can be difficult to adsorb small analytes, or to bind small analytes covalently, to the surfaces of plates, tubes, or the like. A strong, preferably covalent, attachment of low molecular weight moieties is particularly important with surface transverse wave devices, so that the device can be used repetitively without the bound moieties being washed away between individual cycles. The method of the invention addresses this need in the art and provides a simple, reliable method of attaching small analyte molecules to substrate surfaces, such as the mass-sensitive surfaces of piezoelectric surface transverse wave devices.

SUMMARY OF THE INVENTION

Accordingly, the invention is directed to a method for binding low molecular weight analytes to a substrate surface. In a preferred embodiment, the substrate surface is a piezoelectric crystal of a surface transverse wave device; however, as will be explained in detail below, the method is useful in a number of other contexts as well. The method involves coating the substrate surface with a biotin-binding protein such as avidin, covalently binding the analyte of interest, or a functionally equivalent molecule as will be explained below, to biotin, and then providing the biotinylated analyte as a layer on the coated surface.

A further aspect of the invention involves providing a method for determining the presence and/or amount of an analyte in a sample by contacting the surface so prepared, having analyte molecules bound thereto, with a quantitatively detectable analyte-binding moiety, a molecular species which binds covalently or otherwise to the surface-bound analyte, in a sample containing the analyte, or an analyte analog, a molecular species capable of interacting and binding to the analyte-binding moiety in a manner similar to the analyte, in turn enabling quantitation thereof. In a preferred embodiment, this method is carried out in the context of immersing a surface transverse wave device, coated with an analyte as described above, in a solution containing analyte-binding moiety, e.g., an antibody to an antigenic analyte, and either a known or unknown amount of analyte or analyte analog, and evaluating the change in mass loading on the device surface.

In another aspect of the invention, a biotin-analyte complex is provided having the structural formula

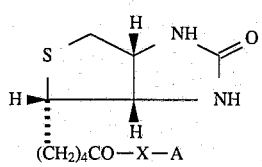

wherein X represents a linking moiety and A represents an analyte having a molecular weight of less than about 1000.

In still another aspect of the invention, a piezoelectric surface transverse wave device is provided in which the binding surface thereof is first coated with a biotin-binding protein as described above, and then coated with a layer of a biotin-bound analyte as will be described in detail herein.

DETAILED DESCRIPTION OF THE INVENTION

Figure 1:
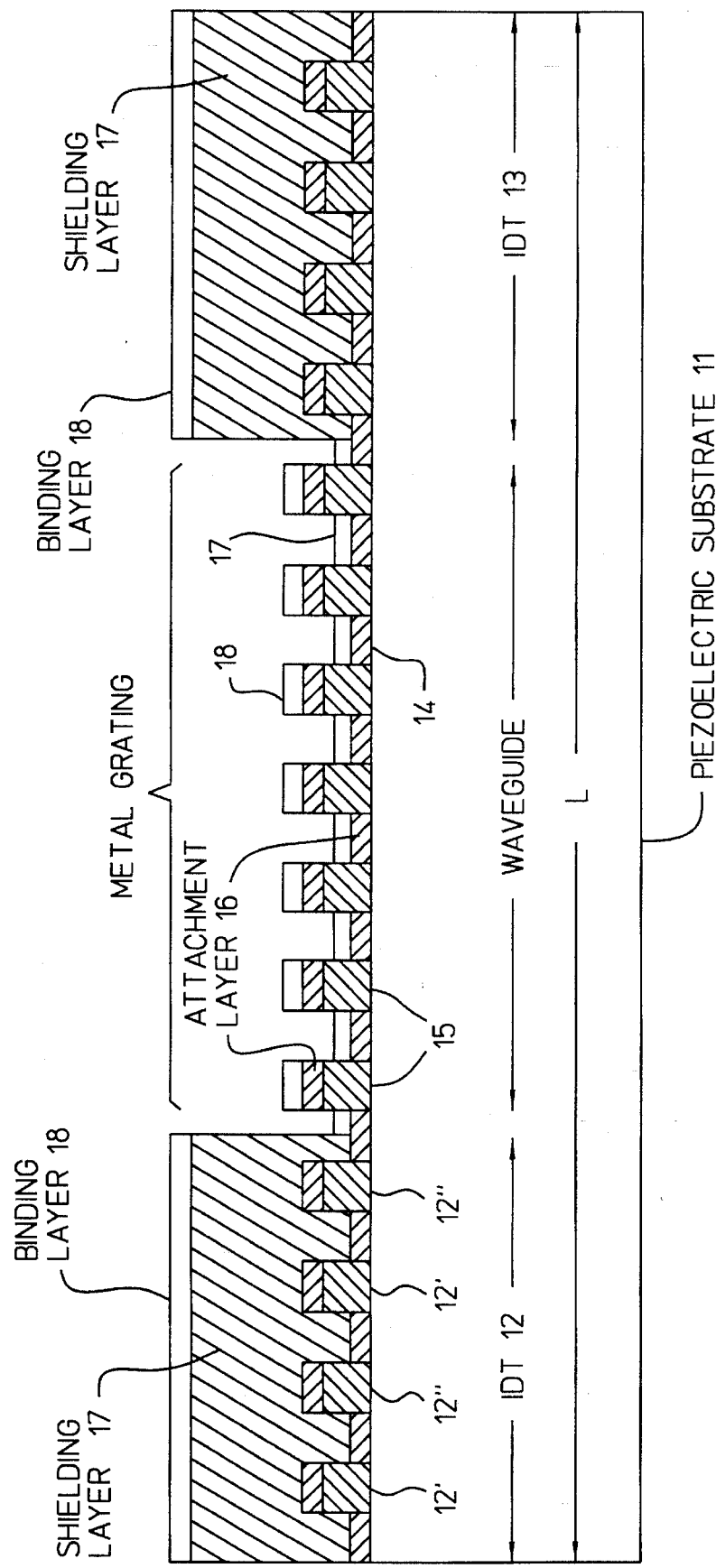
FIG. 1 illustrates in cross-section a surface transverse wave device, as described in commonly owned U.S. Pat. No. 5,130,257 to Baer et al., which may be used in conjunction with the present analyte-binding and diagnostic techniques.

Before the invention is described in detail, it is to be understood that this invention is not limited to specific analytes or coating techniques as such may vary. It is also to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise. Thus, for example, reference to "an analyte" includes mixtures of analytes, reference to "a biotin-binding protein" includes mixtures of two or more such proteins, and the like. In this regard, it is important to note that the techniques of the present invention may be used to quantitate multiple analytes on a binding surface, e.g., as present in a piezoelectric surface transverse wave device.

In this specification and in the claims which follow, reference will be made to a number of terms which shall be defined to have the following meanings:

The term "analyte" as used herein is intended to mean a molecular species to be quantitated. Preferred analytes are low molecular weight, and particularly preferred analytes are environmental analytes having a molecular weight of less than about 1000. The term "environmental analyte" denotes an analyte which is artificially present in the external environment and of general concern with respect to health, safety or the like. As noted above, the analytes are bound to a reactive surface. The presence or amount of analyte in a sample is determined by virtue of binding an analyte-binding moiety, e.g., an antibody in the case of an antigenic analyte, present in the sample to the surface-bound analyte. The term "analyte" is also intended to encompass molecular species which are functionally equivalent to analytes of interest in a particular context. For example, in a competitive immunoassay in which the analyte to be quantitated is an antigen which binds to an antibody present in the sample solution, the term "analyte" includes not only the antigen itself but any species which will bind to the antibody in the same manner and with, in general, a similar degree of affinity as the actual antigen. Thus, the term "analyte" includes analyte analogs, analyte fragments, and the like.

The term "low molecular weight" to describe the analytes of the invention intends a molecular weight of less than about 1000, preferably less than about 600, and most preferably less than about 300.

The term "biotin-binding protein" as used herein is intended to encompass any proteins which will bind to $K_a$ of $10^{14}$ 1 L/M or higher. Such proteins include but are not limited to the egg-white protein avidin, a tetramer containing four identical subunits of molecular weight 15,000, and streptavidin, having an almost identical tetrameric structure, whether naturally occurring, recombinantly produced, or chemically synthesized. When the term "avidin" is used herein, it is to be understood that streptavidin and other biotin-binding proteins are intended as well.

The term "alkylene" to denote the preferred structure of the hydrocarbyl moiety linking biotin to the analyte is used in its conventional sense to refer to a bifunctional saturated branched or unbranched hydrocarbon chain containing from 1 to 24 carbon atoms, and includes, for example, methylene (—$CH_2$—), ethylene (—$CH_2$—$CH_2$—), propylene (—$CH_2$—$CH_2$—$CH_2$—), 2-methylpropylene [—$CH_2$—$CH(CH_3)$—$CH_2$—], hexylene [—$(CH_2)_6$—] and the like. The term "lower alkylene" refers to an alkylene group of one to six carbon atoms, e.g., methylene, ethylene, propylene, and the like. As will be explained below, the alkylene linking moieties may contain one or more substituents or intervening linking groups which do not interfere with the biotin-analyte complexation.

The term "alkenylene" to denote an alternative structure of the hydrocarbyl moiety linking biotin to the analyte is used in its conventional sense to refer to a bifunctional branched or unbranched hydrocarbon chain containing from 2 to 24 carbon atoms and from 1 to 6, typically 1 or 2, double bonds.

The term "alkynylene" to denote still an additional alternative structure of the hydrocarbyl moiety linking biotin to the analyte is used in its conventional sense to refer to a bifunctional branched or unbranched hydrocarbon chain containing from 2 to 24 carbon atoms and from 1 to 6, typically 1 or 2, triple bonds.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, preferably one to four carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

"Halo" or "halogen" refers to fluoro, chloro, bromo or iodo, and usually relates to halo substitution for a hydrogen atom in an organic compound.

"Optional" or "optionally" means that the subsequently described event or circumstance may or may not occur, and that the description includes instances where said event or circumstance occurs and instances where it does not. For example, the phrase "optionally substituted alkylene" means that an alkylene moiety may or may not be substituted and that the description includes both unsubstituted alkylene and alkylene where there is substitution.

The initial step in the analyte-binding process involves coating the surface of a selected substrate with a layer of a specific binding material, i.e., a biotin-binding protein, to provide for a selectively reactive surface. Methods of coating surfaces of various types with avidin or like proteins are well known in the art. The specific method used is not critical and any well-known means for coating a surface with avidin or other biotin-binding proteins may be used. See, for example, Wong, "Chemistry of Protein Conjugation and Cross-Linking," CRC Press, Inc., Boca Raton, Fla., which discloses conventional means for the attachment of a protein to the surface of a solid support.

When a silica support is used, a preferred method involves functionalizing the surface prior to coating with avidin, using a three-step process. As described in co-pending U.S. Patent application Ser. No. 08/041,662, cited above, $SiO_2$ is sputter-deposited to a layer on the order of 100 to 1000 Angstroms thick, resulting in a number of free hydroxyl groups on the silica surface. In the second step, the hydroxyl groups are treated with an organosilane coupling agent to further functionalize the initial layer. The organosilane coupling agent is preferably represented by the formula $R_n SiY_{(4-n)}$ where: Y represents a hydrolyzable group, e.g., alkoxy, typically lower alkoxy, acyloxy, lower acyloxy, amine, halogen, typically chlorine, or the like; R represents a nonhydrolyzable organic radical that possesses a functionality which enables the coupling agent to bond with organic resins and polymers; and n is 1, 2 or 3. One example of such an organosilane coupling agent is 3-glycidoxypropyltrimethoxysilane ("GOPS"), the coupling chemistry of which is well-known in the art. See, for example, Arkins, "Silane Coupling Agent Chemistry," Petrarch Systems Register and Review, Eds. Anderson et al. (1987). Another example of an organosilane coupling agent is (γ-aminopropyl)triethoxysilane. Still other suitable coupling agents are well-known to those skilled in the art. In the third step, the organosilane coupling agent, now covalently bound to the substrate surface, is derivatized, if necessary, to provide for surface reactive groups which will bind the avidin coating. For example, if the organosilane coupling agent provides for surface vicinal diol groups, these can be converted to reactive aldehyde groups by conventional methods (e.g., by reaction with sodium periodate). The reactive aldehyde groups react with the amino groups in avidin to form imines (i.e., Schiff bases, —N=C<). Reduction of the imine with a suitable reducing agent such as sodium cyanoborohydride at suitable pH provides the amine derivative and results in the covalent attachment of the avidin to the surface layer of the piezoelectric surface wave device. Alternatively, if the organosilane coupling agent provides for surface amino groups, these can then react directly with the carboxyl groups present on the avidin to form covalent amide bonds. In this embodiment, it may be desirable to activate the carboxyl groups of the avidin prior to reaction with the surface amine groups.

Still other methods of binding avidin to substrate surfaces are described in G. T. Hermanson et al., "Immobilized Affinity Ligand Techniques," San Diego, CA: Academic Press (1992) at pages 199–202. Examples of such other methods include cyanogen bromide and periodate-induced activation of Sepharose, after which avidin can be directly coupled to the activated surface.

After coating the substrate surface with avidin or like biotin-binding protein, a covalent biotin-analyte complex is prepared which will then bind to the avidin-coated surface. Suitable analytes have molecular weights less than about 1000, preferably less than about 600, and most preferably less than about 300. Preferred analytes are environmental analytes, and are exemplified by but not limited to the following: acetochlor, alachlor, aldicarb, aldicarb sulfone, aldicarb sulfoxide, aldrin, ametrym, 2-aminobenzimidazole, atrazine, benomyl, benzimidazole, 2-benzimidazolyl urea, butachlor, captafol, captan, 3-carbamyl-2,4,5-trichlorobenzoic acid, carbaryl, carbendazim, carbofuran, carbofuran phenol, chlordane, chlorothalonil, desethyl atrazine, desisopropyl atrazine, 3,5-dichloroaniline, dichlorophenols, dichlorprop, didealky atrazine, dieldrin, endosulfan, endrin, EPTC (S-ethyl dipropylthiocarbamate), folpet, heptachlor, hexachlorobenzene, 3-hydroxy-carbofuran, iprodione, 3-ketocarbofuran, 3-ketocarbofuran phenol, MBC, metalaxyl, methomyl, methoprene, metolachlor, 1-naphthol, pentachloronitrobenzene, pentachlorophenol, phthalimide, polychlorinated biphenyl, prometryn, procymidone, propachlor, simazine, simetryne, terbutryn, terbutylazine, 2,4,5,6-tetrachloro-3-cyanobenzamide, tetrachlorohydroquinone, tetrachlorophenols, tetrahydrophthalimide, thiabendazole, thiophanat-methyl, 2,5,6-trichloro-4-hydroxyisophthalonitrile, trichlorophenols, vinciozolin, 2,4-dichlorophenoxyacetic acid ("2,4-D"), 2,4,5-trichlorophenoxyacetic acid ("2,4,5-T"), (4-chloro-2-methylphenoxy) acetic acid ("MCPA") and (4-chloro-2-methylphenoxy) butyric acid ("MCPD"). The covalent biotin-analyte complex may be represented by the general formula

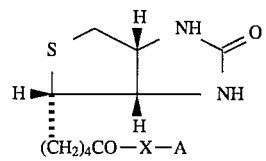

where X is a linking group and A is the analyte. X is typically a $C_1$–$C_{24}$, more typically $C_1$–$C_{12}$, hydrocarbyl linker substituted with 0 to 6, preferably 0–4, substituents selected from the group consisting of lower alkyl, lower alkoxy, hydroxyl, halogen and amino, optionally containing 1 to 6, typically 1–4, —O—, —S—, —NR$^1$— (where R$^1$ is hydrogen or lower alkyl), —CONH—, —(CO)— or —COO— linkages. Generally, X will have an alkylene backbone, although it may also have an alkenylene or alkynylene structure as defined earlier herein.

It may be necessary to functionalize the analyte so that it is capable of reacting with biotin, i.e., by providing an amino, hydroxyl, carboxyl group, or the like, on the analyte. It will be appreciated that techniques for such functionalizations are well known to those skilled in the art of synthetic organic chemistry. For example, taking the environmental analyte atrazine as an example, it may be functionalized by reaction with 1,3-diaminopropane to provide for an alkylamino "handle" as illustrated in the following scheme:

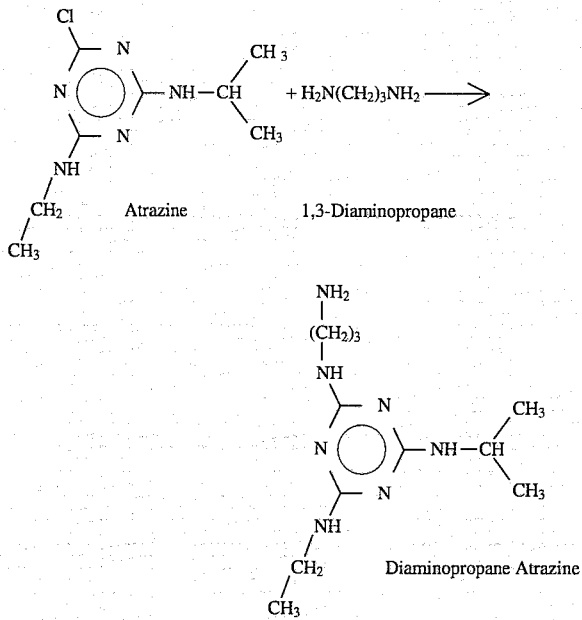

The functionalized atrazine molecule may then couple to biotin itself, in the presence of a suitable coupling agent, or, more typically, or to an activated biotin derivative such as N-hydroxysuccinimide-long chain biotin ("NHS-LC-biotin"), to produce the complex

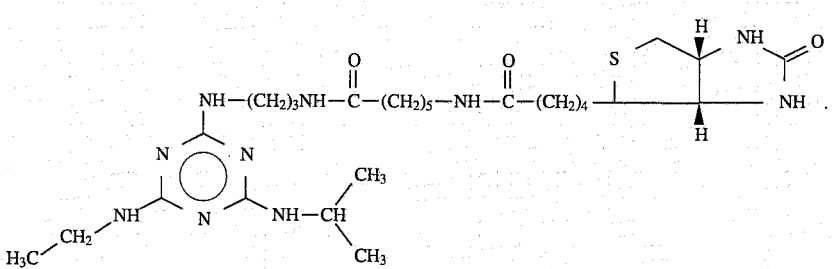

In general, the analyte of interest is coupled to a biotin molecule which has been activated so that it readily reacts with a functional group on the analyte. A variety of activated biotins are commercially available, e.g., from Pierce Chemical Co., Molecular Probes, Sigma, and Vector. Examples of activated biotins include those shown below.

Methods for coupling biotin to various types of molecules are well-known in the art, and the particular method used is not critical. Suitable methods are described, for example, by M. Wilchek et al., in "The Avidin-Biotin Complex in Bioanalytical Applications," Anal. Biochem. 171:1–32 (1988), cited earlier herein. As summarized in the aforementioned reference, illustrative coupling reactions are as follows:

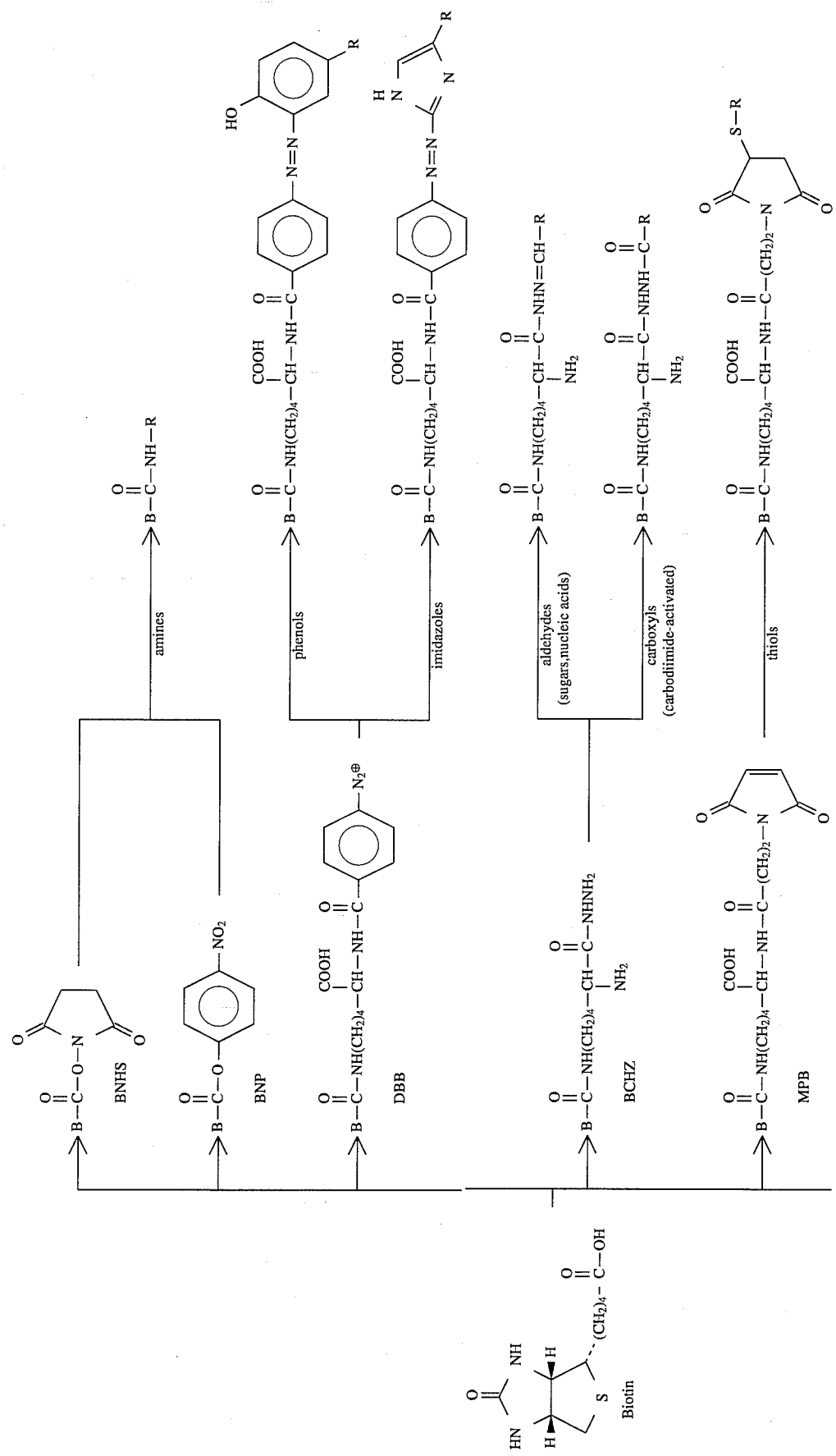

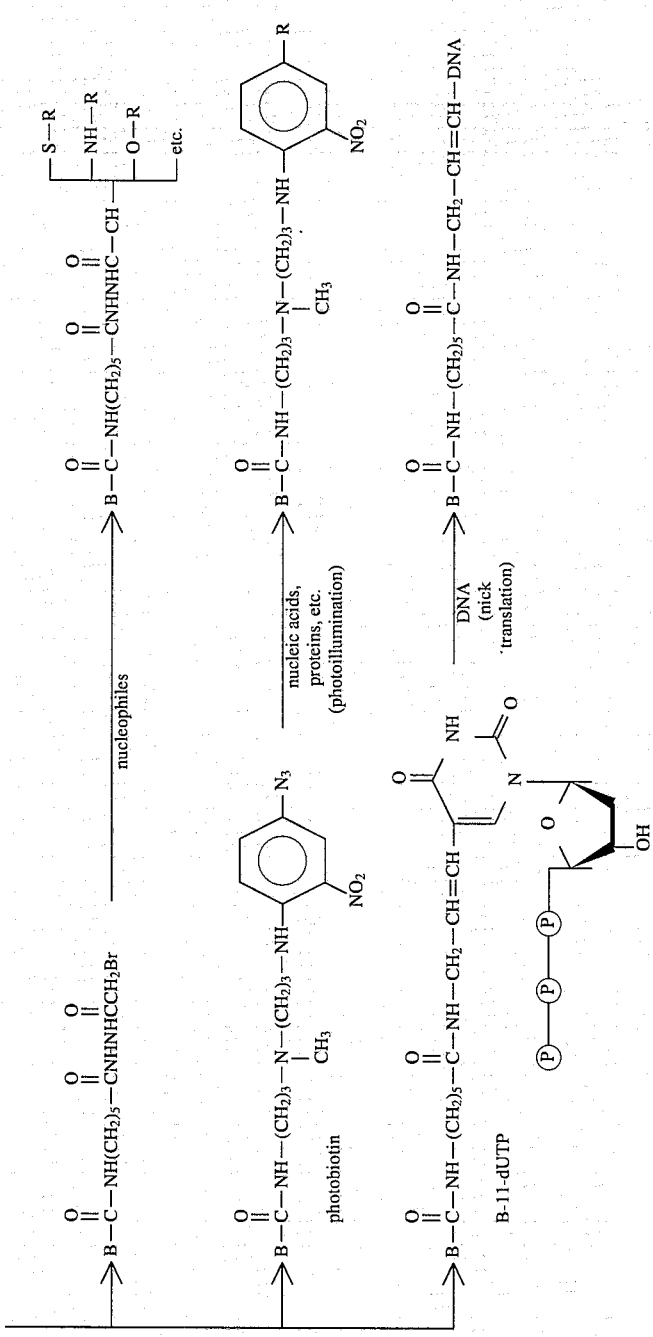

In the above reactions, "B" represents biotin, without the carboxyl group (i.e., it is incorporated into the activated biotin structures on the left side of the reaction schemes), R represents the remainder of the molecule which is not shown, and the abbreviations are as follows: "BNHS," biotin N-hydroxysuccinimide ester; "NP," nitrophenyl; "DBB," p-diazobenzoyl biocytin; "BCHZ," biocytin hydrazide ($N^6$-biotinyl-L-lysine hydrazide); "MBP," 3-(N-maleimido-propionyl) biocytin; "photobiotin," N-(4-azido-2-nitrophenyl)-N'-(N-biotinyl) 3-aminopropyl)-N'-methyl-1,3-propanediamine; "B-11-dUTP," 5[N-(3-aminoallyl) N'-biotinyl 6-aminocaproyl] deoxyuridine 5'-triphosphate.

The covalent biotin-analyte complex is then provided as a coating layer over the reactive surface prepared above, i.e., containing a layer of biotin-binding protein. This is done by dissolving the complex in a suitable solvent system. While it will be appreciated by those skilled in the art that any number of solvents or solvent systems may be used, an example of a particularly preferred solvent system is a combination of water and dimethylformamide. The covalent complex is generally dissolved in the minimum amount of organic solvent necessary to effect solution, and then introduced into water (a typical final concentration of covalent complex is approximately 1 wt. %). This solution is then coated to at least monolayer thickness on the reactive surface prepared above. The quantity of analyte on the surface is then measured by contacting the substrate surface with a quantitatively detectable analyte-binding moiety, i.e., a molecular species which binds to the analyte through a covalent, ionic, or ligand-receptor bond, or by adsorption. The quantity of analyte-binding moiety present on the surface is then evaluated, e.g., by detection of a label present on the moiety, by determination of the mass of the surface-bound moiety, or the like.

In a piezoelectric surface transverse wave device, the substrate surface which is coated, as above, is a piezoelectric crystal binding surface. An example of a piezoelectric surface transverse wave device is described in commonly assigned U.S. Pat. No. 5,130,257 to Baer et al and illustrated in FIG. 1. In FIG. 1, on a piezoelectric substrate 11 having a length L, wherein S and W respectively indicate the spacing and width of the designated component, such as of quartz or lithium niobate ($LiNbO_3$), are formed an input transducer, such as interdigital transducer (IDT) 12 having electrodes 12' and 12", and an output transducer, such as interdigital transducer (IDT) 13. These IDTs have a typical thickness $T_1$ on the order of 0.1–1.0 microns, a width $W_1$ on the order of 1–100 microns and a spacing $S_1$ on the order of 1–100 microns. Reflective gratings are optionally placed at the outside edge of each IDT. These transducers and gratings can be formed by well-known photolithographic techniques.

In general, the material chosen for substrate 11 must be piezoelectric and have specific crystal cuts that enable trapping of surface transverse waves at a surface of the substrate, and should: (1) exhibit low acoustic loss (i.e., have low viscous attenuation); (2) have a high dielectric constant and high electro-mechanical coupling constant to minimize the parasitic electrical effects of fluid loading upon the transducer; and (3) have a low variation of velocity with temperature. Quartz has the advantage of exhibiting a low temperature variation of the acoustic velocity. Lithium niobate has the advantage of better piezoelectric coupling to IDTs 12 and 13. The ST-cut of quartz (typically used for SAW devices) can be used for STW devices by rotating the propagation direction 90 degrees.

On top of surface 14, between IDTs 12 and 13, is formed a metal grating 15 having element width $W_2$ and spacing $S_2$ comparable to the width and spacing of IDTs 12 and 13. This grating traps the transverse acoustic wave to the surface of the substrate. The fingers of the grating can be shortened together with buss-bars to minimize the dielectric effects of the fluid on the performance of the detector.

An attachment layer 16 can be deposited (e.g., by sputtering or evaporation) on top of elements 12, 13 and 14. Layer 16 should bind strongly and be hermetic to protect elements 11 to 15 from attack by chemicals. This layer has a thickness $T_2$ on the order of 10–1,000 Angstroms, and is selected to provide a good binding surface for the reactive layer 18 of biotin-binding protein which is then adapted to bind a layer of biotinylated analyte as described herein.

Layer 18 typically has a thickness $T_4$ on the order of up to several microns.

A thick shielding layer 17 is deposited over IDTs 12 and 13. Shielding layer 17 has a thickness $T_3$ on the order of or larger than the electrode spacing in the IDT.

A preferred embodiment of the claimed method utilizes a plurality of the above-described piezoelectric surface wave devices, which devices are described in copending U.S. Patent application Ser. No. 08/041,662, cited above, which includes: a plurality of piezoelectric surface wave sample devices on which binding surfaces are layered a biotin-binding protein, adapted to bind a layer of a biotinylated analyte, which respond to the presence of the analyte in a sample; and at least one piezoelectric surface wave reference device, on which binding surface is layered a biotin-binding protein, which is not so adapted, which responds to interferences arising from contacting the device with the sample.

While the novel method has been described in conjunction with piezoelectric surface transverse wave devices, it will be appreciated that the method could also be used in conjunction with acoustical, optical, gravimetric, electrochemical, photoelectrochemical, capacitance and thermistor sensors. Gravimetric sensors utilizing piezoelectric crystals include Rayleigh surface acoustic wave devices and Lamb acoustic wave devices as well as the surface transverse wave device. Fiber optic evanescent sensors and evanescent planar waveguide sensors are among the possible optical sensors. Among those in the electrochemical category are potentiometric, amperometric and field-effect transistor ("FET") sensors.

The method of the invention can be used in conjunction with binding analytes to other types of substrates as well, e.g., chromatographic support matrices, silica beads, glass tubes, petri dishes, and the like.

The invention is also useful for measuring a wide variety of analytes. Areas of application include, but are not limited to, environmental sensing, in vitro diagnostics, food and agriculture quality assurance and control, research, and medicine. Examples for use in environmental sensing include the determination of contaminants in natural bodies of water, the evaluation of drinking water quality, determination of pesticides in a water sample, determination of soil and sludge contamination, monitoring of industrial streams, and the like.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

The following examples are put forth so as to provide those of ordinary skill in the art with a complete disclosure and description of how to use the method of the invention, and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

EXAMPLE 1

Preparation of avidin-coated silica substrate:

(a.) Silanization of silica substrate: A 10% solution of 3-glycidoxypropyltrimethoxysilane ("GOPS"), pH 3.0, was prepared using 2.5 ml GOPS (Aldrich Chemical Co.), 20 ml isopropanol, 2.5 ml $H_2O$, and 1 ml acetic acid. A silica substrate pretreated with $SiO_2$ was exposed to the solution. Hydrolysis was allowed to proceed for one hour, and 0.25 ml triethylamine (Aldrich Chemical Co.) was then added as a catalyst. An additional hour was allowed for binding. The substrate surface was then rinsed 3–5X with distilled water and allowed to dry in vacuo or under helium, or in a mechanical oven at 110° C. for 10 minutes.

(b.) Oxidation of epoxide or diol groups on GOPS: A 0.1% periodate solution was prepared using 1 g $NaIO_4$, 200 ml $H_2O$, and 800 ml acetic acid. The silanized substrate was then incubated for 30 minutes at room temperature with this solution, and then washed with water.

(c.) Incubation of substrate with avidin: The washed substrate of part (b.) was then incubated with a solution of avidin D (Vector) in borate buffered saline ("BBS"), pH 8.5, at a concentration of 0.1 mg/ml, and mixed by gentle inversion at 4° C. for 20–24 hours.

(d.) Reduction of Schiff's base to a stable reduction product: Following the incubation of step (c.), a 0.1 M solution of $NaBH_3CN$ in pH 6 phosphate buffer (0.1 M) was added at three fifteen-minute intervals to give a final $NaBH_3CN$ concentration of 0.1 M. The substrate surface was then rinsed with PBS, pH 7.0.

Synthesis and binding of atrazine-biotin complex:

(a.) Synthesis of diaminopropane-atrazine: A solution of 400 mg of atrazine (Ultra-Scientific) and 00 equivalents (~10 ml) of 1,3-diaminopropane (Sigma) in 40 ml of n-propanol was refluxed for 1 hour. The reaction mixture was followed by TLC using Kodak Chromagram Sheet 13181 Silica Gel and eluted in ether:hexane/1:1.

The mixture was then concentrated in a rotary evaporator overnight until the volume was reduced to 10 ml. The reduced sample was transferred to a separatory funnel and made basic with 100 ml 0.5 N NaOH. The aqueous phase was extracted 4X with methylene chloride ($CH_2Cl_2$).

The combined organic phases were washed with 50 ml of saturated NaCl and then dried with $MgSO_4$. The mixture was filtered, the solvent removed on a rotary evaporator, and the residue dried under vacuum for 2 days. The final yield from the starting material (400 mg) was 421 mg which was 90% of the theoretical yield. The resultant material was clear, yellow and very viscous.

To confirm the identity of the adduct of atrazine with diaminopropane, the product was analyzed using electrospray mass spectrometry. The mass spectrum showed a single peak at 254.1 amu, indicating that the major product has the correct molecular weight for atrazine that has been modified with diaminopropane.

Following the mass spectroscopic analysis, the diaminopropane-atrazine was reacted with NHS-LC-Biotin, (N-hydroxysuccinimide-long chain biotin, Pierce). Diaminopropane-atrazine (10 mg), as prepared above, was dissolved in 40 µl of dimethylformamide to which was added 20 mg NHS-LC-Biotin reagent dissolved in 1 ml of 40 mM $NaHCO_3$, pH 8.5. The mixture was incubated for 2 hours at 4° C. and then applied to STW devices previously derivatized with avidin D (Vector Labs) using the procedure described above. This incubation requires at least two hours for maximum binding of the biotinylated atrazine but can also proceed overnight.

Evaluation of STW Devices

Figure 2:
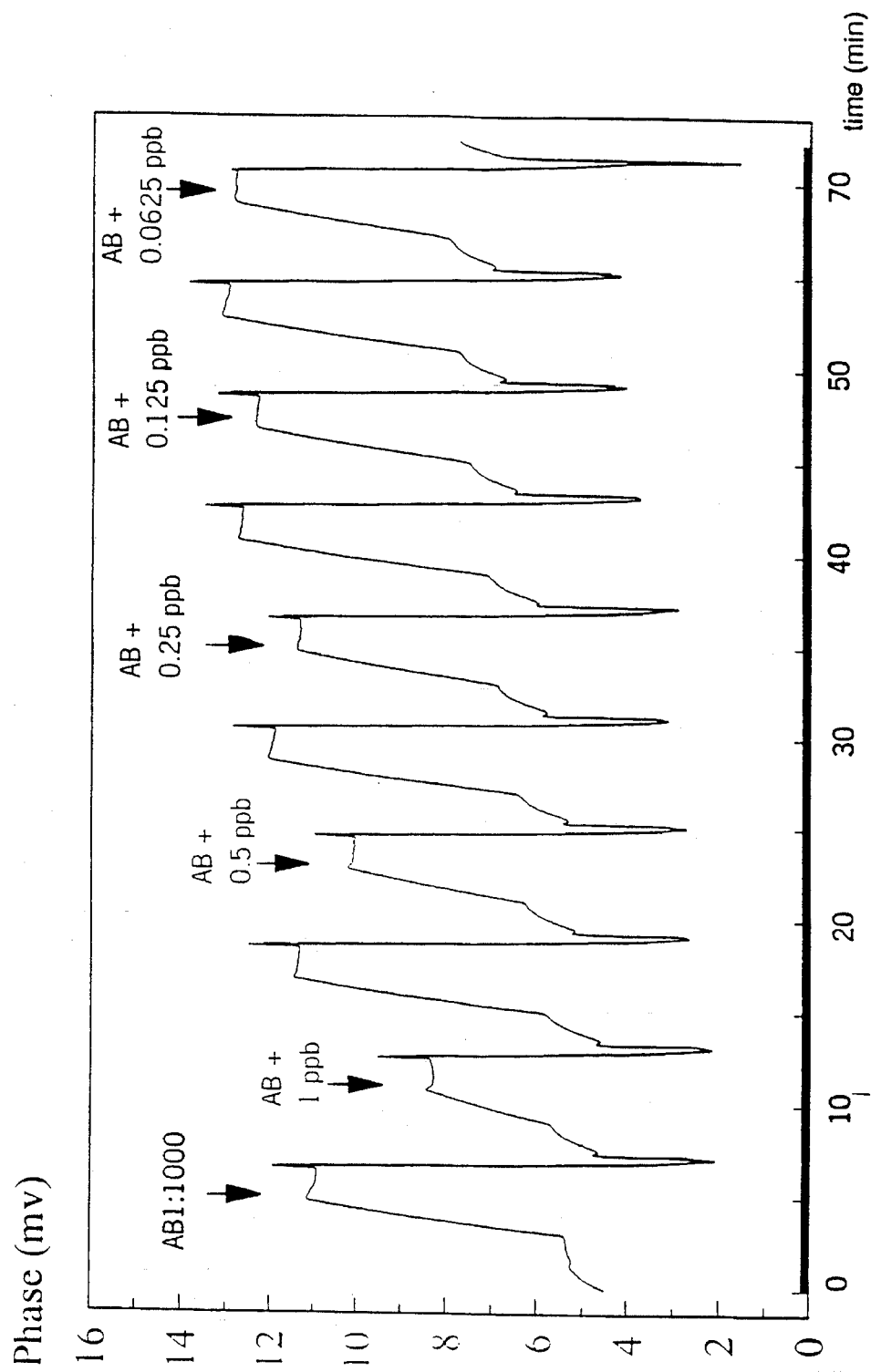
FIG. 2 is a graph deriving from the experimental work set forth in Example 1, illustrating the detection of atrazine antibody using an atrazine-coated piezoelectric surface transverse wave device prepared using the method of the invention.

The devices were then tested in the biosensor measurement configuration. The graph of FIG. 2 demonstrates the feasibility of the invention. The graph represents data taken from an experiment in which the biotinylated-atrazine has been immobilized to the STW device. Using a competitive immunoassay format, atrazine in the presence of a constant concentration of atrazine antibody was detected in real time and without the use of labeled reagents.

The experiment proves that the derivatized atrazine was successfully immobilized to the STW device and that it was derivatized in a way that did not adversely affect the recognition sites on the atrazine molecule.

Example 2

Synthesis and binding of biotinylated analog of carbendazim

The biotinylated analog of carbendazim is synthesized by first reacting 2-aminobenzimidazole with succinic anhydride. The 2-succinamidobenzimidazole thereby produced is then reacted with biocytin hydrazide ($N^6$-biotinyl-L-Lysine hydrazine). The resulting biotinylated analog is applied to STW devices as described in Example 1.

Example 3

Synthesis and binding of biotinylated analog of 2,4-dichlorophenol

The biotinylated analog of 2,4-diclorophenol is synthesized by reacting 2,4-dichlorophenol with p-diazobenzoyl-biocytin. The resulting biotinylated analog of 2,4-dichlorophenol is applied to STW devices as described in Example 1.

Example 4

Synthesis and binding of biotinylated analog of 2,4-dichlorophenoxyacetic acid

The biotinylated analog of 2,4-dichlorophenoxyacetic acid is synthesized by reacting 2,4-dichlorophenoxyacetic acid with biocytin hydrazide ($N^6$-biotinyl-L-Lysine hydrazine). The resulting biotinylated analog of 2,4-diclorophenoxyacetic acid is applied to STW devices as described in Example 1.

We claim:

1. A method for binding an environmental analyte having a molecular weight of less than about 1000 to a surface of a piezoelectric substrate, comprising:

coating the surface with a layer of a specific binding material comprised of a biotin-binding protein to provide a reactive surface;

covalently binding the analyte, either directly or indirectly, to biotin, to provide a biotin-analyte complex; and coating the reactive surface with the biotin-analyte complex such that the analyte is bound thereto.

2. The method of claim 1, wherein the biotin-binding protein is selected from the group consisting of avidin and streptavidin.

3. The method of claim 1, wherein the analyte is selected from the group consisting of acetochlor, alachlor, aldicarb, aldicarb sulfone, aldicarb sulfoxide, aldrin, ametrym, 2-aminobenzimidazole, atrazine, benomyl, benzimidazole, 2-benzimidazolyl urea, butachlor, captafol, captan, 3-carbamyl-2, 4,5-trichlorobenzoic acid, carbaryl, carbendazim, carbofuran, carbofuran phenol, chlordane, chlorothalonil, desethyl atrazine, desisopropyl atrazine, 3,5-dichloroaniline, dichlorophenol, dichlorprop, didealky atrazine, dieldrin, endosulfan, endrin, EPTC, folpet, heptachlor, hexachlorobenzene, 3-hydroxycarbofuran, iprodione, 3-ketocarbofuran, 3-ketocarbofuran phenol, methyl benzimidazole carbamate (MBC), metalaxyl, methomyl, methoprene, metolachlor, 1-naphthol, pentachloronitro-benzene, pentachlorophenol, phthalimide, polychlorinated biphenyl, prometryn, procymidone, propachlor, simazine, simetryne, terbutryn, terbutylazine, 2,4,5,6-tetrachloro-3-cyanobenzamide, tetrachlorohydroquinone, tetrachlorophenol, tetrahydrophthalimide, thiabendazole, thiophanat-methyl, 2,5,6-trichloro-4-hydroxyisophthalonitrile, trichlorophenol, vinciozolin, 2,4-dichlorophenoxyacetic acid, 2,4,5-trichlorophenoxyacetic acid, (4-chloro-2methylphenoxy) acetic acid ("MCPA") and (4-chloro-2methylphenoxy)butyric acid ("MCPB").

4. The method of claim 3, wherein the analyte is atrazine.

5. The method of claim 1, wherein the analyte is bound directly to biotin.

6. The method of claim 1, wherein the analyte is bound to biotin through a linking group.

7. The method of claim 6, wherein the biotin-analyte complex has the structural formula

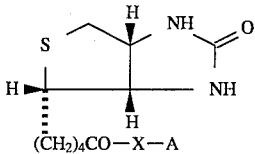

wherein X is the linking group and A is the analyte.

8. The method of claim 7, wherein X is a $C_1$–$C_{24}$ hydrocarbyl linking group substituted with 0 to 6 substituents selected from the group consisting of lower alkyl, lower alkoxy, hydroxyl, halogen and amino, optionally containing 1 to 6 —$NR^1$—, —CONH—, —(CO)— or —COO— linkages where $R^1$ is hydrogen or lower alkyl.

9. The method of claim 8, wherein X is a $C_1$–$C_{12}$ alkylene linking group substituted with 0 to 4 substituents selected from the group consisting of lower alkyl, lower alkoxy, hydroxyl, halogen and amino, optionally containing 1 to 4 —O—, —NH—, —CONH— or —(CO)— linkages.

10. The method of claim 1, wherein the biotin-analyte complex has the structural formula

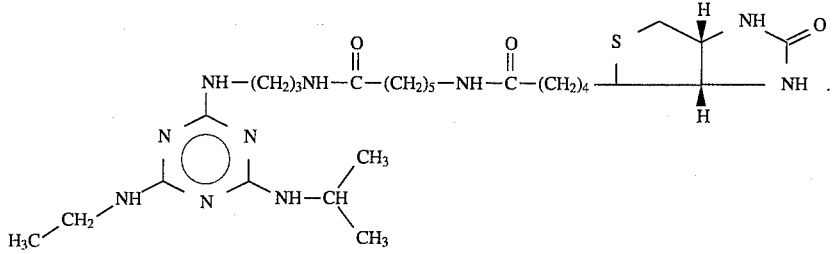

11. The method of claim 1, wherein the substrate is a piezoelectric surface transverse wave device.

12. A method for quantitating an environmental analyte having a molecular weight of less than about 1000, comprising:

(a) providing a piezoelectric substrate comprising surface-bound analyte by
 (i) coating the surface with a layer of a protein which specifically binds biotin, to provide a reactive surface,
 (ii) covalently binding the analyte, either directly or indirectly, to biotin, to provide a biotin-analyte complex, and
 (iii) coating the reactive surface with the biotin-analyte complex to provide the surface with bound analyte;

(b) contacting the surface-bound analyte with
 (i) a specific binding partner which specifically binds to the analyte and an analog thereof, and
 (ii) a first liquid sample suspected of containing the analyte,
such that the formation of a first specific binding complex that comprises the specific binding partner and the surface bound analyte produces a first detectable mass on the piezoelectric substrate, wherein the first detectable mass is inversely proportional to the amount of the analyte in the first liquid sample;

(c) contacting the surface-bound analyte with
 (i) the specific binding partner, and
 (ii) a second liquid sample containing a standard comprising a known concentration of the analyte or the analog thereof, such that the formation of a second specific binding complex that comprises the specific binding partner and the surface bound analyte produces a second detectable mass on the piezoelectric substrate, wherein the second detectable mass is inversely proportional to the amount of the standard in the second liquid sample; and (d) determining the quantity of the analyte in the first liquid sample by correlating the first detectable mass produced on the piezoelectric substrate by the first specific binding complex to the second detectable mass produced on the piezoelectric substrate by the second specific binding complex.

13. The method of claim 12, wherein the biotin-binding protein is selected from the group consisting of avidin and streptavidin.

14. The method of claim 12, wherein the analyte is selected from the group consisting of acetochlor, alachlor, aldicarb, aldicarb sulfone, aldicarb sulfoxide, aldrin, ametrym, 2-aminobenzimidazole, atrazine, benomyl, benzimidazole, 2-benzimidazolyl urea, butachlor, captafol, captan, 3-carbamyl-2,4,5-trichlorobenzoic acid, carbaryl, carbendazim, carbofuran, carbofuran phenol, chlordane, chlorothalonil, desethyl atrazine, desisopropyl atrazine, 3,5-dichloroaniline, dichlorophenol, dichlorprop, didealky atrazine, dieldrin, endosulfan, endrin, EPTC, folpet, heptachlor, hexachlorobenzene, 3-hydroxycarbofuran, iprodione, 3-ketocarbofuran, 3-ketocarbofuran phenol, methyl benzimidazole carbamate MBC, metalaxyl, methomyl, methoprene, metolachlor, 1-napthol, pentachloronitrobenzene, pentachlorophenol, phthalimide, polychlorinated biphenyl, prometryn, procymidone, propachlor, simazine, simetryne, terbutryn, terbutylazine, 2,4,5,6-tetrachloro-3-cyanobenzamide, tetrachlorohydroquinone, tetrachlorophenol, tetrahydrophthalimide, thiabendazole, thiophanat-methyl, 2,5,6-trichloro-4-hydroxyisophthalonitrile, trichlorophenol, vinciozolin, 2,4-dichlorophenoxyacetic acid, 2,4,5-trichlorophenoxyacetic acid, (4-chloro-2-methylphenoxy)acetic acid ("MCPA") and (4-chloro-2methylphenoxy)butyric acid ("MCPB").

15. The method of claim 14, wherein the analyte is atrazine.

16. The method of claim 12, wherein the analyte is bound directly to biotin.

17. The method of claim 12, wherein the analyte is bound to biotin through a linking group.

18. The method of claim 17, wherein the biotin-analyte complex has the structural formula

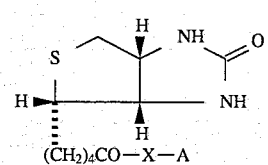

wherein X is the linking group and A is the analyte.

19. The method of claim 18, wherein X is a $C_1$–$C_{24}$ hydrocarbyl linking group substituted with 0 to 6 substituents selected from the group consisting of lower alkyl, lower alkoxy, hydroxyl, halogen and amino, optionally containing 1 to 6 —O—, —S—, —NR$^1$—, —CONH—, —(CO)— or —COO— linkages where $R^1$ is hydrogen or lower alkyl.

20. The method of claim 19, wherein X is a $C_1$–$C_{12}$ alkylene linking group substituted with 0 to 4 substituents selected from the group consisting of lower alkyl, lower alkoxy, hydroxyl, halogen and amino, optionally containing 1 to 4 —O—, —CONH— or —(CO)— linkages.

21. The method of claim 13, wherein the biotin-analyte complex has the structural formula

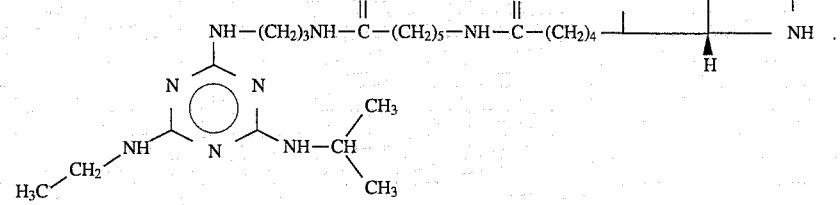

22. A biotin-analyte complex having the structural formula

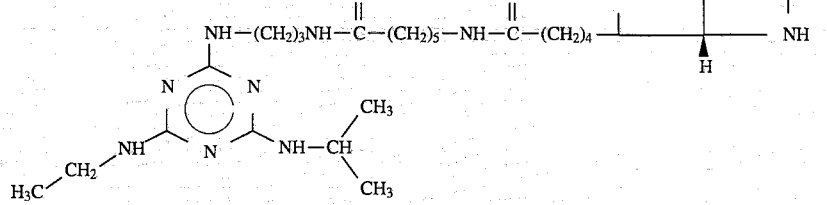

wherein X is a $C_1$–$C_{12}$ alkylene linking group substituted with 0 to 4 substituents selected from the group consisting of lower alkyl, hydroxyl, halogen and amino, optionally containing 1 to 4 —O—, —NH—, —CONH— or —(CO)— linkages and A is an analyte having a molecular weight of less than about 1000.

23. The biotin-analyte complex of claim 22, wherein the biotin-analyte complex has the structural formula

* * * * *